(12) United States Patent
Morinaka

(10) Patent No.: US 7,569,022 B2
(45) Date of Patent: Aug. 4, 2009

(54) BODY ORTHOSIS

(75) Inventor: Shigeru Morinaka, Ehime (JP)

(73) Assignee: Shiyomi Prosthetic Mfg., Inc. (JP)

( * ) Notice: Subject to any disclaimer, the term of this patent is extended or adjusted under 35 U.S.C. 154(b) by 1148 days.

(21) Appl. No.: 10/416,431

(22) PCT Filed: Nov. 13, 2001

(86) PCT No.: PCT/JP01/09918

§ 371 (c)(1),
(2), (4) Date: May 9, 2003

(87) PCT Pub. No.: WO02/39934

PCT Pub. Date: May 23, 2002

(65) Prior Publication Data

US 2004/0030275 A1    Feb. 12, 2004

(30) Foreign Application Priority Data

Nov. 15, 2000    (JP)    ............................. 2000-347505

(51) Int. Cl.
*A61F 5/00*    (2006.01)
(52) U.S. Cl. ................ 602/16; 602/5; 602/20; 602/23; 602/27
(58) Field of Classification Search .............. 602/5, 602/16, 20, 23, 27–29
See application file for complete search history.

(56) References Cited

U.S. PATENT DOCUMENTS

| | | | |
|---|---|---|---|
| 3,731,323 A | 5/1973 | Glancy | |
| 4,433,679 A | 2/1984 | Mauldin et al. | |
| 5,022,391 A | 6/1991 | Weidenburner | |
| 5,052,379 A * | 10/1991 | Airy et al. | 602/16 |
| 5,328,446 A | 7/1994 | Bunnell et al. | |
| 5,472,412 A | 12/1995 | Knoth | |
| 5,549,712 A | 8/1996 | Gammer et al. | |
| 5,873,847 A | 2/1999 | Bennett et al. | |
| 6,171,272 B1 | 1/2001 | Akita et al. | |
| 6,280,404 B1 | 8/2001 | Morinaka et al. | |

FOREIGN PATENT DOCUMENTS

| | | |
|---|---|---|
| DE | 41 01 021 A1 | 7/1991 |
| EP | 635247 | 1/1995 |
| EP | 0 641 550 A1 | 3/1995 |
| FR | 2766359 A | 1/1999 |
| JP | 1-133911 | 9/1989 |
| JP | 09-103443 | 4/1997 |
| JP | 11-290360 | 10/1999 |
| WO | 95/01769 A | 1/1995 |
| WO | WO97/13487 | 4/1997 |
| WO | 00/06059 A | 2/2000 |

* cited by examiner

*Primary Examiner*—Kim M Lewis
(74) *Attorney, Agent, or Firm*—Kilpatrick Stockton LLP

(57) ABSTRACT

A body orthosis having a pair of body protective members adjacent to each other in a vertical direction, in which one of the body protective member 1 is constituted so as to rotate freely with respect to the other body protective member 2, the body orthosis including rotational load setting means 8 for setting a rotational load in one rotational direction of the rotatably constructed body protective member 2 larger than a rotational load in the other rotational direction.

10 Claims, 17 Drawing Sheets

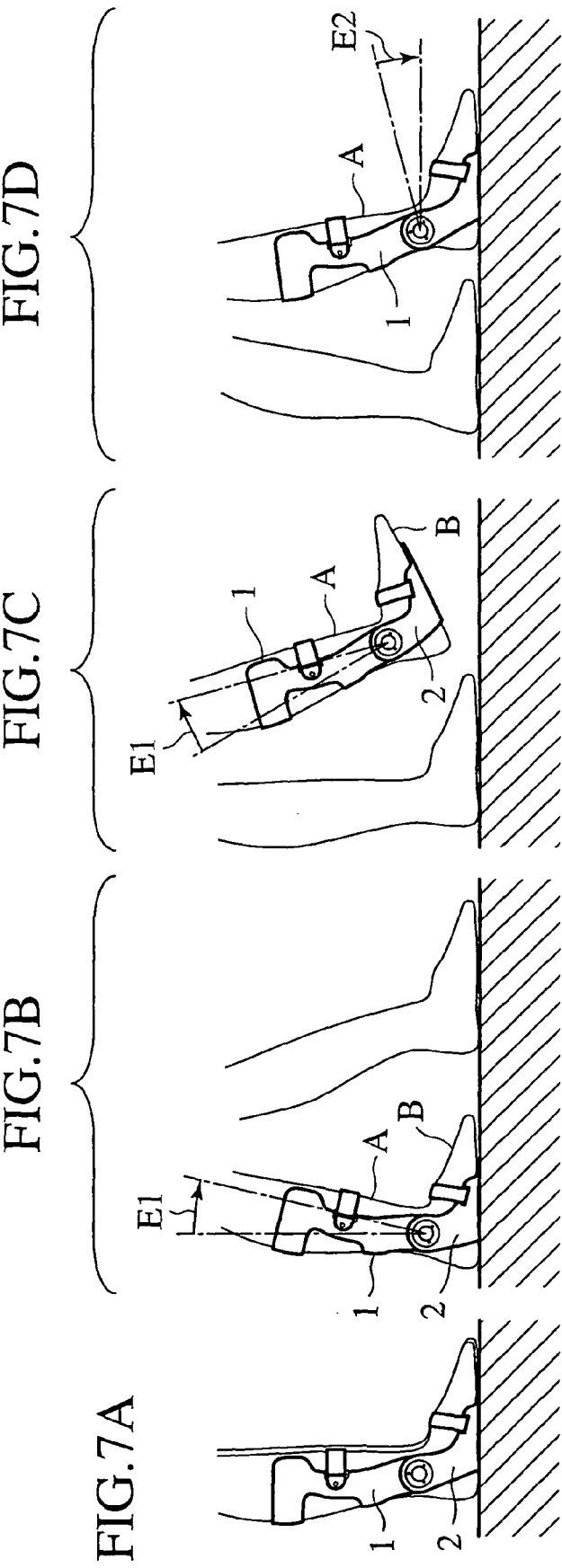

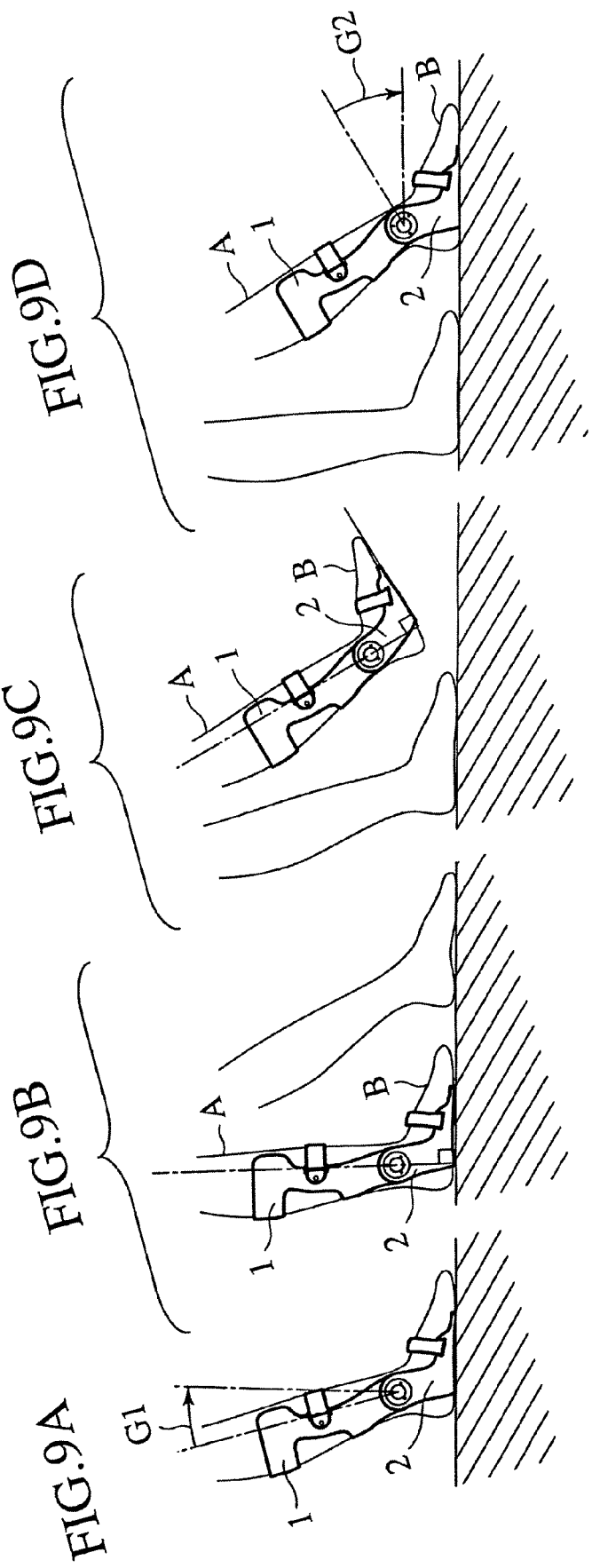

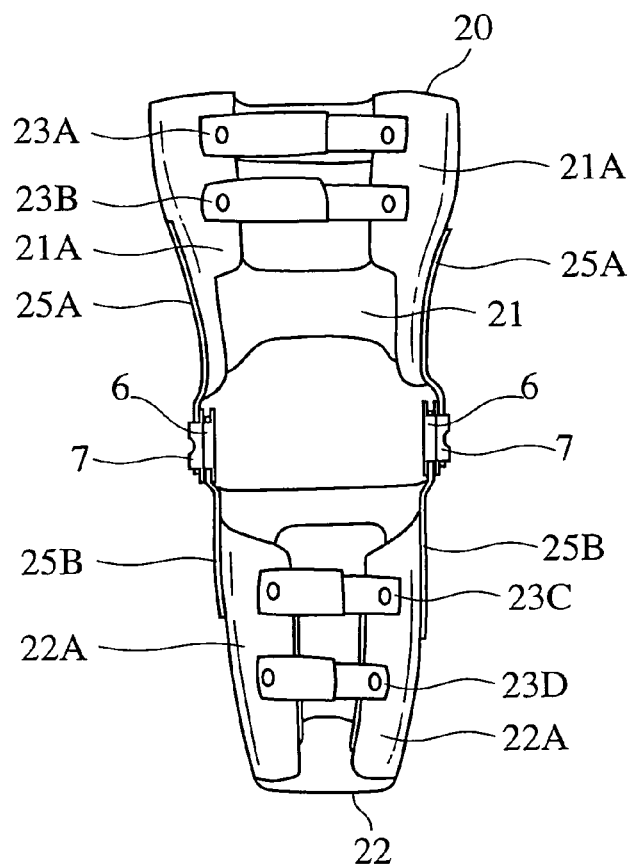
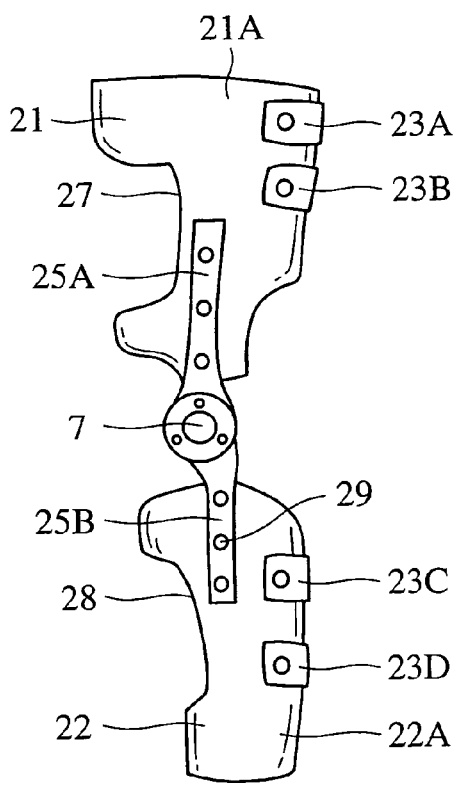

BODY ORTHOSIS

TECHNICAL FIELD

The present invention relates to a body orthosis especially effective as a body corrective orthosis for talipes equinovarus, the body orthosis having a pair of body protective members adjacent to each other in a vertical direction, in which one of the body protective members is constituted so as to rotate around an axial center in a direction perpendicular to the adjacent direction thereof with respect to the other body protective member.

BACKGROUND ART

Talipes equinovarus (clubfoot) means a disorder of a walking function, which causes stumbling easily by stubbing a toe against the ground during walking. This is because inward bending of a foot directs its sole inward, and impossibility of controlling an ankle causes a tiptoe side of the foot (referred to toe, hereinafter) to droop downward.

In order to prevent the stumbling during walking, a toe is corrected upward generally to prevent the drooping downward of the toe. Various types of body orthoses have been proposed for the purpose of correction. As shown in FIG. 5C, a state of a foot positioned parallel to a horizontal direction orthogonal to a leg of a posture parallel to a vertical direction (indicated by a solid line) is set as a normal state. A case of lifting the foot around a malleolus (not shown) from the normal state as indicated by a virtual line (chain double-dashed line) is called dorsiflexion, while a case of lowering the foot from the normal state is called plantar flexion.

In the conventional body orthosis, for example, against an upper body protective members adjacent to each other in upper and lower directions, a lower body protective member is rotatably constructed. The lower body protective member is set to be rotatable only within a predetermined angle (e.g., 45°) to the dorsiflexion side from the normal state. Thus, dorsiflexion is carried out while plantar flexion from the normal state is prevented.

In the case of walking on a flat land by using the conventional body orthosis, a leg is slightly inclined forward immediately before the leg of a healthy side is stepped forward to lift a foot of the body protective member side (see FIG. 7B). Thus, simultaneously with the lifting of the foot, the lower body protective member rotated to the dorsiflexion side is returned to the normal state by weight of the foot, making it possible to reduce stumbling more compared with the case of the drooped toe. However, in walking on a downward slope, the body protective member of the foot side (lower side) need to be rotated to the plantar flexion side against the body protective member of the leg side (upper side). With the above-described constitution, however, plantar flexion cannot be carried out, resulting in unstable walking of a forward-inclined posture. Thus, walking of a near natural state becomes difficult. Moreover, in walking on an upward slope, by landing the foot, the lower body protective member loading and supporting the foot can be subjected to dorsiflexion. However, when the foot in the state of dorsiflexion was lifted, the lower body protective member was returned to a horizontal posture by the weight of the foot, causing the toe to touch the slope and stumble. Moreover, by changing the constitution to one having a rotational angle for enabling plantar flexion on the downward slope, walking can be carried out on the downward slope. However, walking from the downward slope to the flat land or the upward slope is impossible with this constitution. Thus, it has been extremely difficult to handle the body orthosis.

DISCLOSURE OF THE INVENTION

The present invention was made in consideration of the above described situation, and it is an object of the invention to provide a body orthosis for enabling walking of a near natural state without any limits on planar flexion or dorsiflexion.

In order to achieve the above-described object, a body orthosis of the present invention is characterized in that the body orthosis having a pair of body protective members adjacent to each other in a vertical direction, in which one of the body protective members in constituted so as to rotate freely with respect to the other body protective member, the body orthosis including rotational load setting means for setting a rotational load in one rotational direction of the rotatably constructed body protective member larger than a rotational load in the other rotational direction.

Thus, by setting a rotational load to the plantar flexion side larger than that to the dorsiflexion side, when the landed foot is lifted, the foot can be held by the body orthosis at an angle of the foot immediately before the lifting. Moreover, a load applied by a part of weight caused by the landing of the foot is converted into a rotating force for rotating the body protective member. Accordingly, even when a large rotational load is set, the body protective member can be smoothly rotated.

The body protective member includes a sole plate for loading and supporting at least a part of a sole, and a leg protective plate for protecting at least a part of a leg, and side ends adjacent to these members are connected to each other by the rotational load setting means, thus constructing a lower limb orthosis.

When walking is carried out by using the body protective member composed of the left protective plate and the sole plate, the sole plate is rotated by a load applied at the time of landing the sole plate so as to set its bottom surface parallel to the ground, and when the sole plate is lifted, a renge of the rotational load is set so as to maintain the sole plate and the leg protective plate in states immediately before the lifting.

By setting the rotational load as described above, it is possible to not only prevent contact of the toe with the slope to stumble when the foot is lifted, but also smoothly rotate the sole plate by a load (a part of weight) applied at the time of landing when the sole plate is landed.

The leg protective plate includes a facies posterior cruris cuff for protecting a calf, and a calcaneus portion in the rear side of the sole plate and an Achilles' tendon portion in a lower end rear side of the facies posterior cruris cuff are formed to be open.

The calcaneus portion in the rear side of the sole plate and the Achilles' tendon portion in the lower end rear side of the facies posterior cruris cuff, which cause no problems in strength, are formed to be open type. Accordingly, not only weight can be made light, but also the shoe can be easily put on. Moreover, flexibility of the sole plate and the facies posterior cruris cuff can be adjusted.

By setting the rotational center of the facies posterior cruris cuff substantially equal to the upper-and-lower height position of the foot joint axis of hominal physiology, the foot joint axis of the human body can be brought into rough coincidence with the rotational center of the facies posterior cruris cuff or the rotational center of the sole plate. Thus, the foot joint axis of the human body can be moved more easily.

By forming an opening in the center of the upper and lower sides of the facies posterior cruris cuff, weight saving thereof can be realized, and flexibility can be improved.

The fixing member is provided to fix the human body to the facies posterior cruris cuff or the sole plate over the left and right front ends of the facies posterior cruris cuff or the left and right upper ends of the sole plate. Accordingly, it is possible to prevent falling-off of the body orthosis in walking.

The rotational load setting means is made of the one-way bearing provided in the rotary shaft portion of the rotatably constructed body protective member. Accordingly, a rotational load to one side (e.g., dorsiflexion side) can be removed as much as possible, and a rotational load to the other side (e.g., plantar flexion side) can be set to a range for preventing rotation of the sole plate caused by the weight of the foot placed on the sole plate.

When walking using the body orthosis including the sole plate for loading and supporting at least a part of a sole, and a leg protective plate for protecting at least a part of a leg, the one-way bearing provided in a rotary shaft portion of the leg protective plate to rotate the sole plate by a load applied at the time of landing the sole plate so as to set its bottom surface parallel to the ground in walking, and maintain the sole plate and the leg protective plate in states immediately before lifting when the sole plate is lifted.

As described above, a rotational load to one side (e.g., dorsiflexion side) can be removed as much as possible, and a rotational load to the other side (e.g., plantar flexion side) can be set to a range for preventing rotation of the sole plate caused by the weight of the foot placed on the sole plate. Thus, without any limitations on dorsiflexion or plantar flexion, walking can be carried out in a much more natural state.

The body orthosis of the present invention may be installed beforehand in the shoe. Since the loading portion or the like are housed beforehand in the shoe, the body orthosis can be worn without discomfort and can even be used for exercise or the like.

Furthermore, the body orthosis can be constructed in such a manner that the protective plates of the upper and front arm portions are connected to each other by the rotational load setting means. The body orthosis can be also constructed in such a manner that the protective plates of the thigh and the lower thigh are connected to each other by the rotational load setting means.

BRIEF DESCRIPTION OF THE DRAWINGS

FIG. 7A is a view showing a state where both feet set in line with each other in walking on a flat road by the body orthosis of the first embodiment of the present invention.

FIG. 7B is a view showing a state where a left foot is stepped forward in walking on the flat road by the body orthosis of the first embodiment of the present invention.

FIG. 7C is a view showing a state immediately before a right foot is stepped forward and landed in walking on the flat road by the body orthosis of the first embodiment of the present invention.

FIG. 7D is a view showing a landed state of the right foot stepped forward in walking on the flat land by the body orthosis of the first embodiment of the present invention.

FIG. 9A is a view showing a state where both feet are set in line with each other in walking on a downward slope by the body orthosis of the first embodiment of the present invention.

FIG. 9B is a view showing a state where the left foot is stepped forward in walking on the downward slope by the body orthosis of the present invention.

FIG. 9C is a view showing a state immediately before the right foot is stepped forward and landed in walking on the downward slope by the body orthosis of the first embodiment of the present invention.

FIG. 9D is a view showing a landed state of the right foot stepped forward in walking on the downward slope by the body orthosis of the first embodiment of the present invention.

FIG. 11B is a front view showing the second embodiment of the present invention.

FIG. 11C is a side view showing the second embodiment of the present invention.

BEST MODES FOR CARRYING OUT THE INVENTION

First Embodiment

Figure 1:
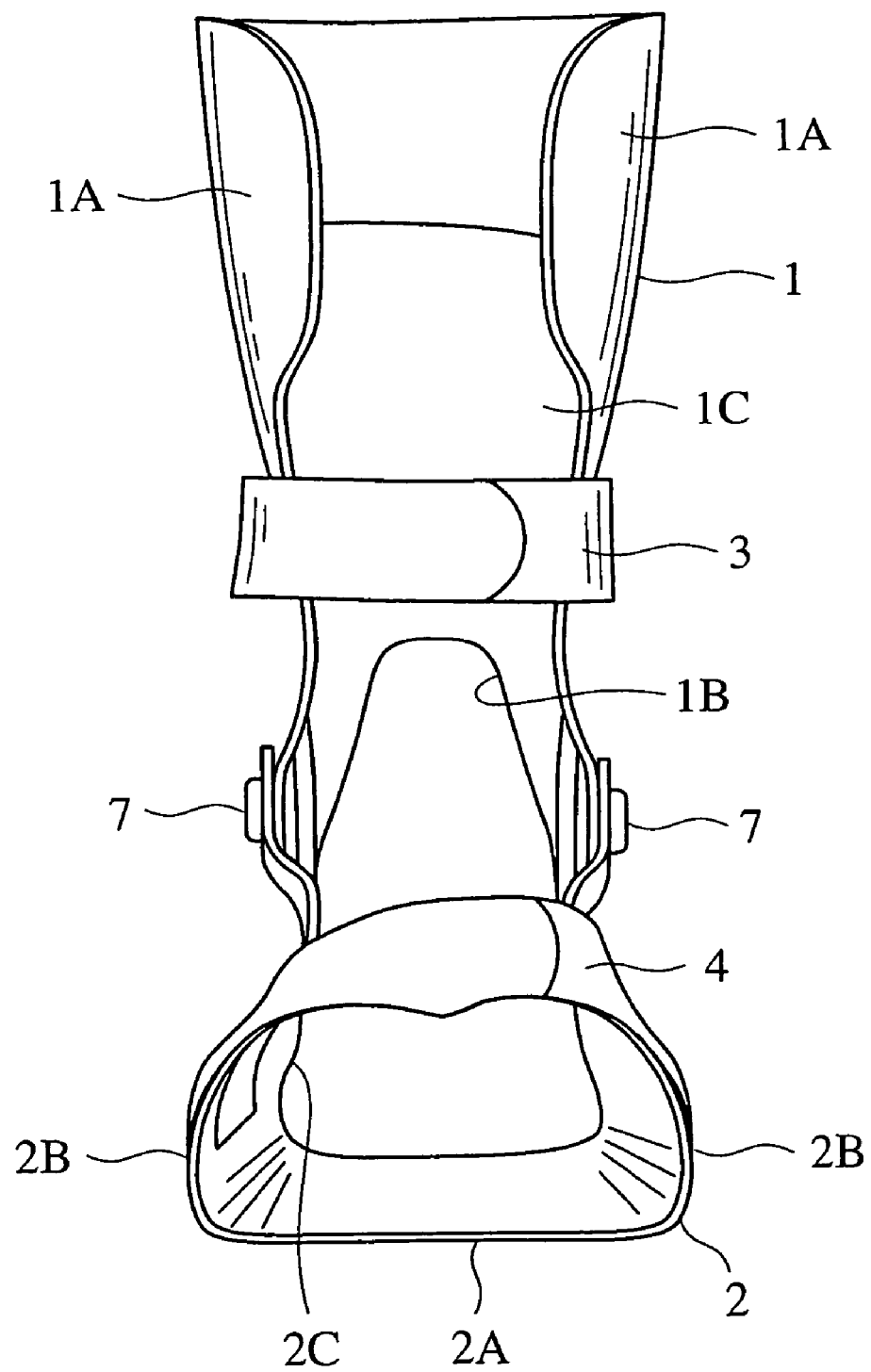
FIG. 1 is a front view of a body orthosis according to a first embodiment of the present invention.
Figure 2:
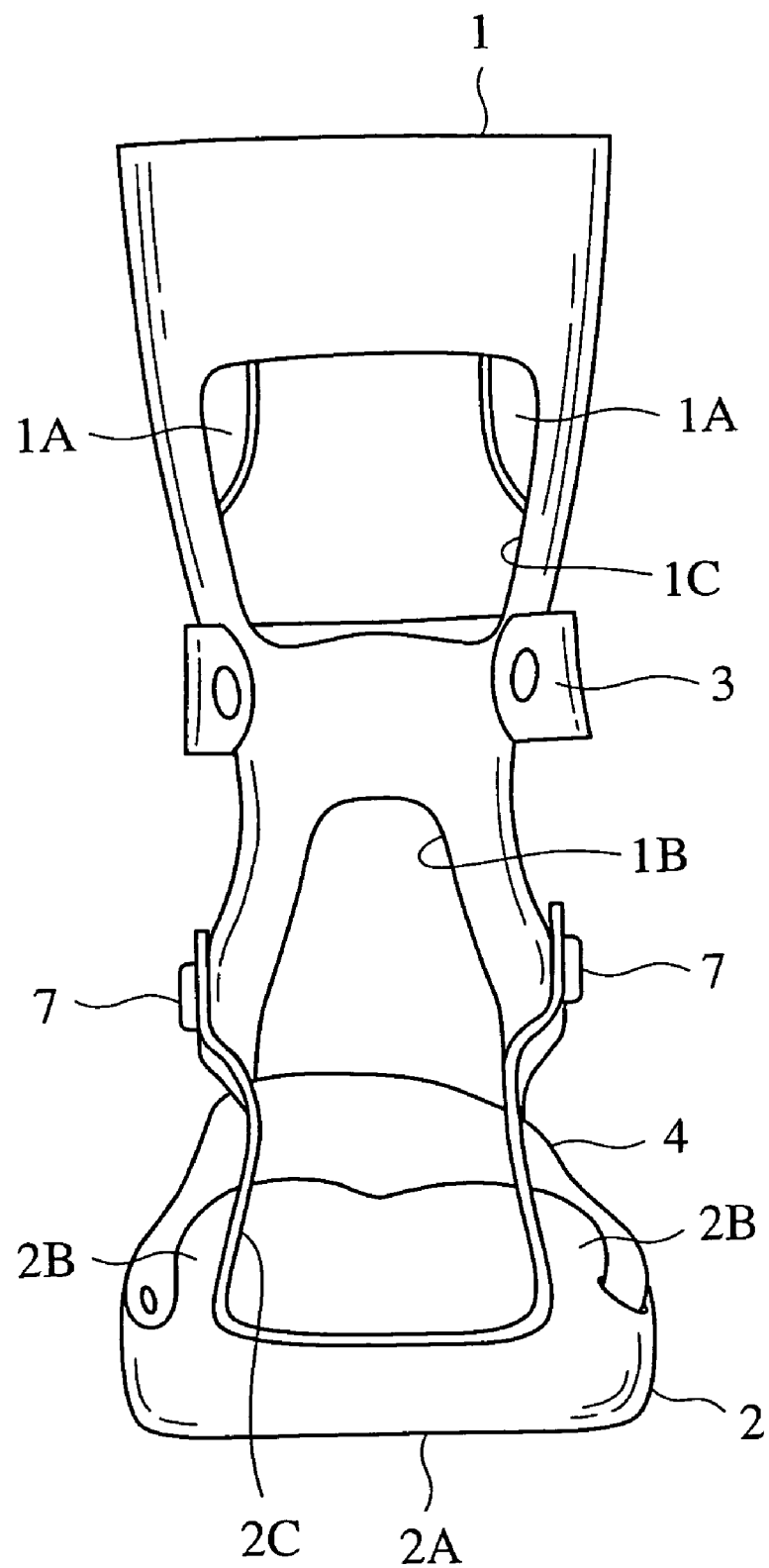
FIG. 2 is a rear view of the body orthosis according to the first embodiment of the present invention.
Figure 3:
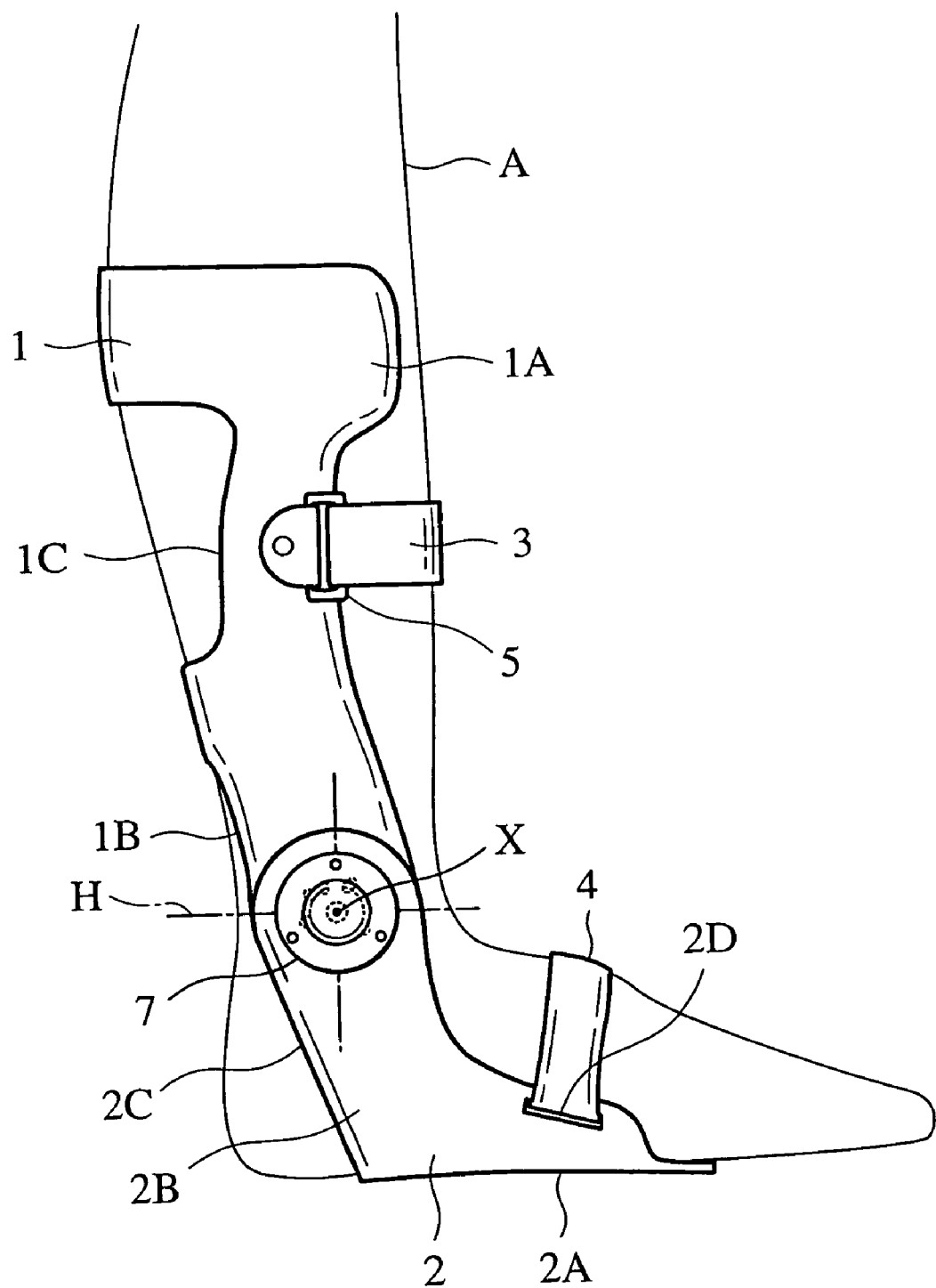
FIG. 3 is a side view of the body orthosis loaded on a lower limb according to the first embodiment of the present invention.

FIGS. 1 to 3 show a body orthosis according to a first embodiment of the present invention. This body orthosis includes two body protective members as main constitutional members. These two members are a facies posterior cruris cuff (leg protective plate) 1 provided with a pair of left and right flared portions 1A and 1A formed bent in a near circular-arc shape when seen from a plane to protect a calf in a rear surface of a shank, and extended forward in an upper end side to cover a part of the shank, and a sole plate 2 nearly U-shaped when seen from a front, provided with a loading portion 2A having a horizontal surface to load and support a foot (part below an ankle), and rising portions 2B and 2B rising from both left and right sides of the loading portion 2A. The facies posterior cruris cuff 1 and the sole plate 2 adjacent to each other in upper and lower directions are connected so as to be rotated around a horizontal axial center. A lower limb below a knee can be fixed to the body orthosis by two belts 3 and 4 shown in the drawing. The belts 3 and 4 as the fixing members both made of hook-and-loop fasteners, which can adjust fastening position continuously. These belts may be made of rubber belts, cords or the like. The belts may even be omitted when the facies posterior cruris cuff 1 and the sole plate 2 themselves have holding forces to hold the lower limb. One end of the belt 3 is fixed to a front end of one transverse side of the facies posterior cruris cuff 1. Ring-shaped metal fittings 5 are fixed to a front end of the other transverse side of the curst rear cuff 1 to get a tip of the belt 3 through. One end of the belt 4 is fixed to an upper end of one transverse side of the sole plate 2. A hole 2D is formed in an upper end of the other transverse side of the sole plate 2 to pass a tip of the belt 4.

The facies posterior cruris cuff 1 and the sole plate 2 are made of various synthetic resins such as polyethylene or by partially mixing those various synthetic resins with other substances such as synthetic rubber and metal to have flexibility. Accordingly, fatigue by long-time use causes no deformation, deterioration and the like even while weight saving thereof is realized. In addition, advantages including capability of satisfactorily absorbing a twisting load received from the body in walking, and capability of restoring an original shape when no loads are applied are provided. However, materials other than the synthetic resins can be used.

As shown in FIG. 1, Achilles' tendon portion 1B in a lower end rear side of the facies posterior cruris cuff 1, and a calcaneus portion 2C in a rear side of the sole plate 2 are formed to be open. Accordingly, the entire body orthosis can be reduced in weight, and a shoe can be easily put on. Moreover, the flexibility of the facies posterior cruris cuff 1 and the sole plate 2 can be adjusted. In the drawing, the shoe is omitted. Reference numeral 1C shown in the drawing denotes an opening portion formed nearly in a center of the upper and lower directions of the facies posterior cruris cuff 2, which enables the entire body orthosis to be reduced more in weight.

Description will be made for support structures for rotatably supporting both left and right sides of the lower end of the facies posterior cruris cuff 1, and both left and right sides of the upper end of the sole plate 2. Note that the left and right sides have identical support structures, therefore only one side will be described.

Figure 6:
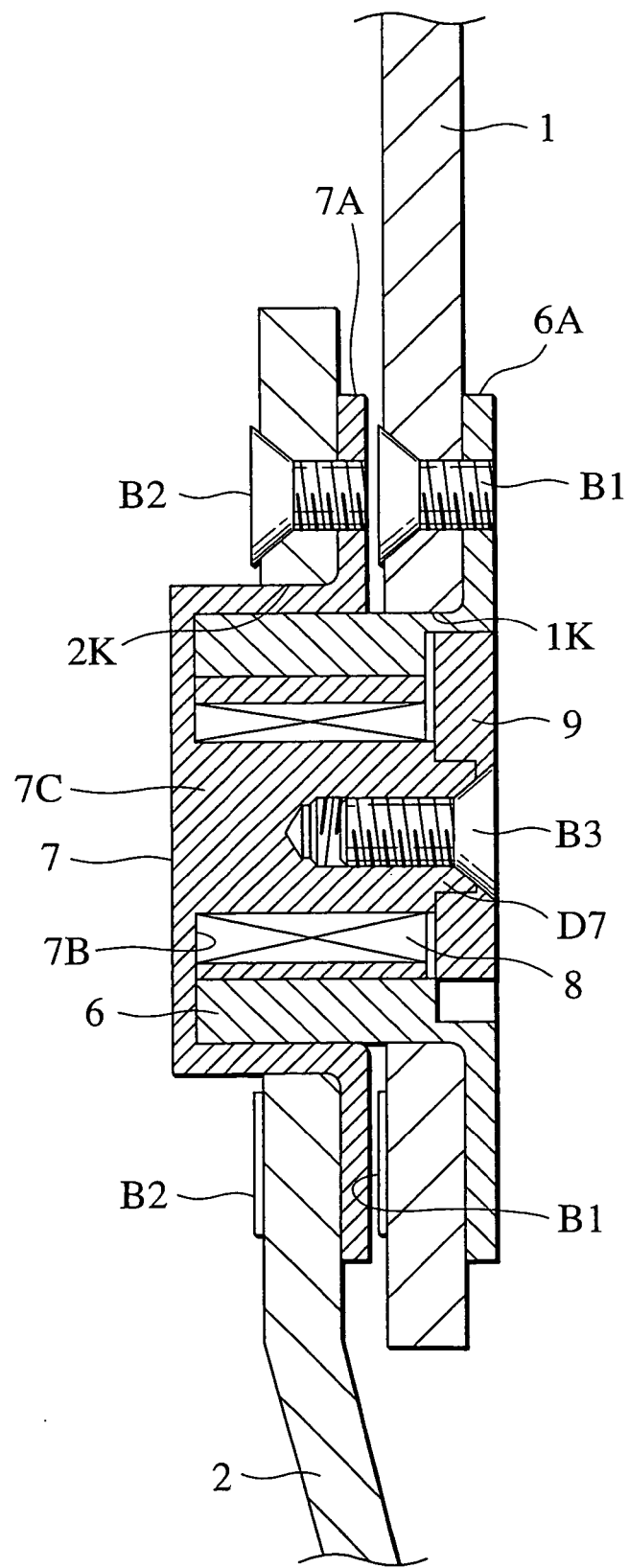
FIG. 6 is a sectional view showing a rotary portion of a body protective member according to the first embodiment of the present invention.

As shown in FIG. 6, circular openings 1K are formed in both left and right sides of the lower part of the facies posterior cruris cuff 1. An inner side cylindrical member 6 made of metal (any material can be used as long as it has rigidity, such as a synthetic resin) and having a flange 6A in one end is inserted from inside into the opening 1K. The flange 6A and the facies posterior cruris cuff 1 are fixed to each other by a plurality of screws B1. Moreover, a circular opening 2K is formed in the upper end of the sole plate 2. An outer member 7 circular in outer shape, made of metal (any material can be used as long as it has rigidity, such as a synthetic resin) and having a flange 7A and an annular and circular concave portion 7B is inserted from inside into the opening 2K. The flange 7A and the sole plate 2 are fixed to each other by a plurality of screws B2. Then, an annular one-way bearing 8 as rotational load setting means is fitted around a circular rotary shaft portion 7C formed in a center of the outer member 7. By the fitting-around of the one-way bearing 8, space is partially used in the concave portion 7B, and the inner side cylindrical member 6 is fitted in a remaining space of the concave portion 7B. Moreover, a later-described stopper 9 fitted in a protruded portion 7D formed in one end of an axial direction of the rotary shaft portion 7C is fixed to the protruded portion 7D by one screw B3. By providing the one-way bearing 8, a rotational load applied to one rotational direction, i.e., a dorsiflexion direction for subjecting the sole plate 2 to dorsiflexion, can be set equal to 0, or near 0. For smoother walking, it is optimum to set a rotational load applied to the other rotational direction, i.e., in a plantar flexion direction for subjecting the sole plate 2 to plantar flexion, equal to a range for maintaining the sole plate 2 and the facies posterior cruris cuff 1 in states immediately before lifting when the sole plate 2 is lifted. However, a rotational load can be set to any range as long as the sole plate 2 and the facies posterior cruris cuff 1 can be maintained in states immediately before lifting when the sole plate 2 is lifted, and the sole plate 2 can be rotated to take a posture having its bottom surface set parallel to or along a ground plane (ground) by a load applied from a leg when the sole plate 2 is landed. The inner side cylindrical member 6 and the outer side member 7 may be omitted, the one-way bearing 8 may be attached to one of the sole plate 2 and the facies posterior cruris cuff 1, and both may be made rotatable. The one-way bearing 8 is used as the rotational load setting means. However, various bearings, friction units or the like for setting a rotational load of one direction larger than that of the other direction can be used.

As shown in FIG. 3, upper and lower height positions H of a hominal physiology foot joint axis (or talocrural joint axis) are set equal to the same height as that of a rotational center X of the facies posterior cruris cuff 1, and the rotational center is set in a position intersecting a vertical line shown in FIG. 3, i.e., in a rough center position of a back and forth direction. This setting of the rotational center X of the facies posterior cruris cuff 1 shown in the drawing is optimum. However, the rotational center X may be set in a slightly shifted position.

Figure 4A:
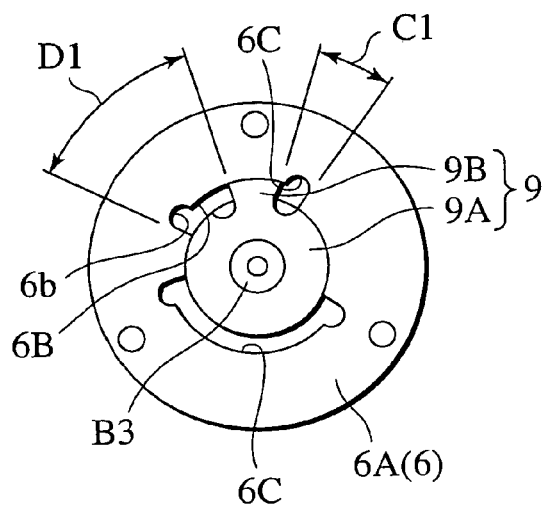
FIG. 4A is a front view showing a relation between a stopper and an inner side cylindrical member.

As shown in FIG. 4A, the stopper 9 includes a disk portion 9A slid into contact with the cylindrical member side end surface (diameter direction inner end surface) of the flange 6A of the inner side cylindrical member 6 to guide the same following rotation of the inner side cylindrical member 6, and a nearly reverse-trapezoidal protruded portion 9B protruded in a diameter direction in a part of an outer peripheral edge of the disk portion 9A. Long grooves 6B and 6C different from each other in length are formed in two places of an outer peripheral direction in the cylindrical member side end (diameter direction inner end) of the flange 6A of the inner side cylindrical member 6. The protruded portion 9B is inserted into one of the long grooves 6B and 6C, i.e., the long groove 6B (upper side in the drawing). Accordingly, from a state of a foot joint of 0°, i.e., a state of nearly 90° between a foot B and a leg A (indicated by a solid line) as shown in FIG. 4C, the sole plate 2 can be rotated by 45° (angle range of D1 shown in FIGS. 4A and 4C) to a dorsiflexion side with 20° to a plantar flexion side. In both ends of the long groove 6B or 6C, notched portions 6b or 6c are formed in circular-arc shapes toward the diameter outer side. Thus, smooth rotation can be made on both ends even without accurately forming the long grooves 6B and 6C to both ends thereof.

Figure 4B:
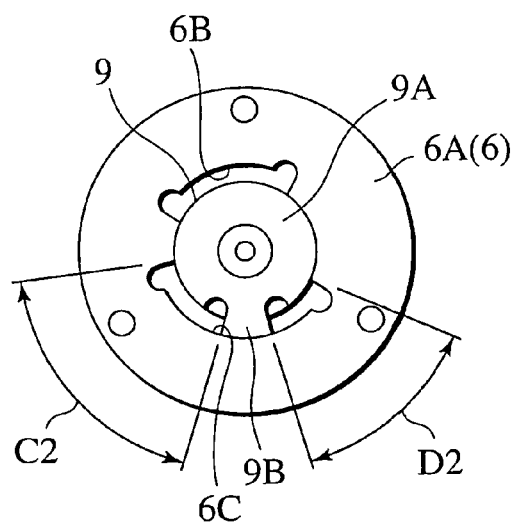
FIG. 4B is a view showing a state where the stopper shown in FIG. 4A is rotated by 180°.
Figure 4C:
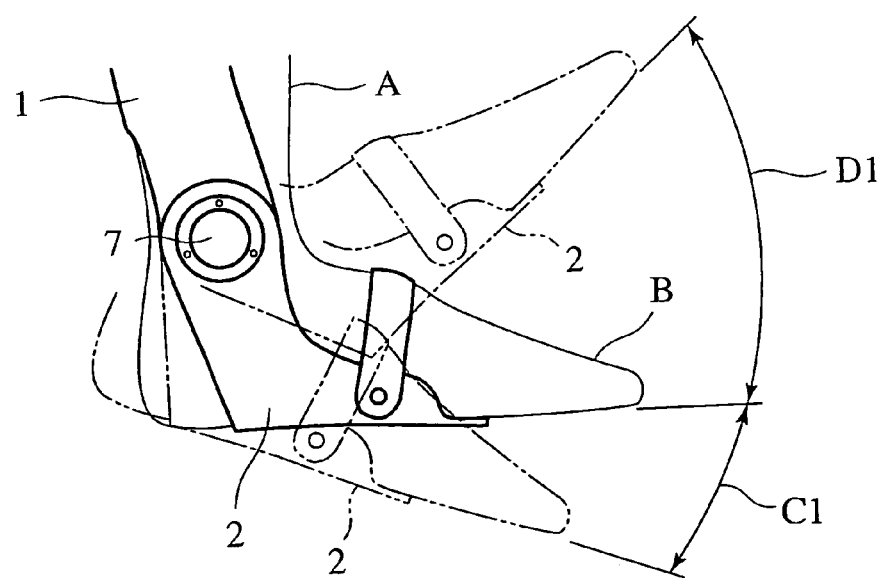
FIG. 4C is an explanatory view showing a range of rotation when the stopper of FIG. 4A is used.

As shown in FIG. 4B, the stopper 9 may be rotated by 180° to insert the protruded portion 9B into the other long groove 6C (lower side in the drawing). Accordingly, from the state of the foot joint of 0° similar to the above, the sole plate 2 can be rotated by 45° (angle range of D2 shown in FIG. 4B) to the dorsiflexion side with 65° (angle range of C2 shown in FIG. 4B) to the plantar flexion side.

Figure 5A:
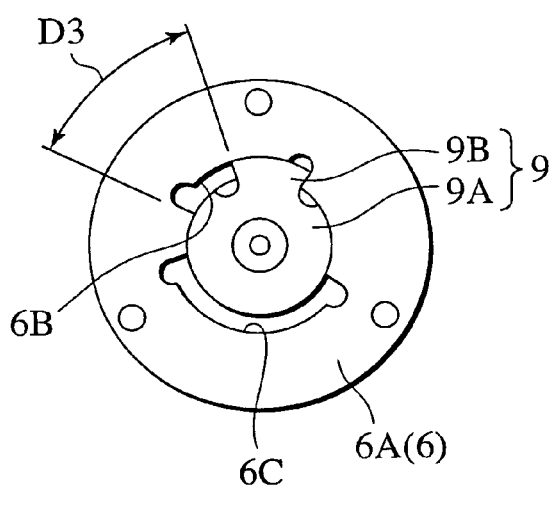
FIG. 5A is a front view showing a relation between a stopper wider than the stopper shown in FIG. 4 and the inner side cylindrical member.
Figure 5B:
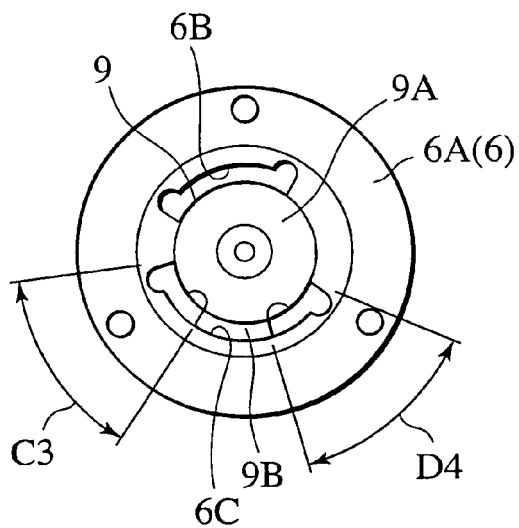
FIG. 5B is a view showing a state where the wide stopper shown in FIG. 5A is rotated by 180°.
Figure 5C:
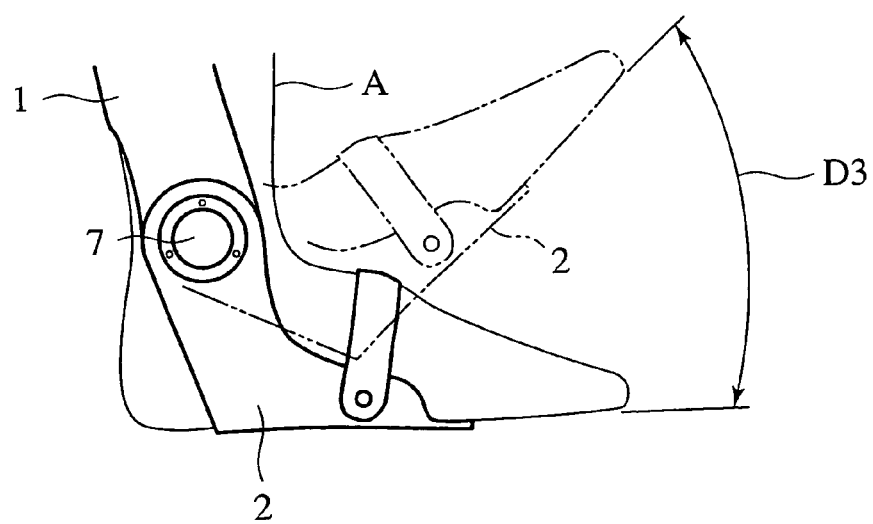
FIG. 5C is an explanatory view showing a range of rotation when the stopper of FIG. 5A is used.

FIG. 5A shows a stopper having an outer peripheral direction dimension (width dimension) of a protruded portion larger (wider) than that of the protruded portion 9B of the stopper 9. From the state of the foot joint of 0° similar to the above, the sole plate 2 can be rotated by 45° (angle range of D3 shown in FIGS. 5B and 5C) only to the dorsiflexion side.

The stopper 9 shown in FIG. 5A may be rotated by 180° to insert the protruded portion 9B in the other long groove 6C (lower side in the drawing). Accordingly, from the state of the foot joint of 0° similar to the above, the sole plate 2 can be rotated by 45° (angle range of D4 shown in FIG. 5B) to the dorsiflexion side with 45° (angle range of C3 shown in FIG. 5B) to the plantar flexion side.

Note that, a movable range of the foot joint of the human body is less than 45° for both dorsiflesion and plantar flexion (less than 35° in some cases). By setting a rotational angle to 45° as described above, a state similar to a free state of no angle limitations is achieved for the human body. Moreover, the rotational angle limitation is not limited to the above-described set angle. The rotational angle limitation may be necessary for changes according to a symptom degree (level) of the talipes equinovarus or the like. However, no problems occur when the stopper 9 is omitted, and performed in a completely free state.

Description will be made for the case of walking with the body orthosis constructed in the foregoing manner loaded on an affected part. First, in the case of walking on a flat road having a level ground, from a state where a left foot of a healthy side and a right foot wearing the body orthosis are in line with each other when seen from a side as shown in FIG. 7A, the left foot of the healthy side is stepped forward. Then, as shown in FIG. 7B, a leg A of the right foot of the orthosis side is inclined by 15° from a vertical side (angle of E1 in FIG. 7B). In this case, a rotational load to the dorsiflexion side is 0 or near 0, and thus the facies posterior cruris cuff 1 can be rotated to set an angle of the leg A smoothly. Subsequently, when the right foot of the orthosis is lifted to be stepped forward, as shown in FIG. 7C, the right foot can be moved while the posture immediately before the lifting (posture of the leg A of the right foot being inclined forward by 15° from a vertical posture). Thus, a toe of the right foot is prevented from drooping forward to be caught on the ground. When the right foot lifted from the ground is landed on the ground, a load applied from the foot at the time of landing rotates the sole plate 2 by 15° (angle of E2 in FIG. 7D) to the plantar flexion side, thereby changing a posture of the sole plate 2 so as to set its bottom surface parallel to the ground.

Figure 8A:
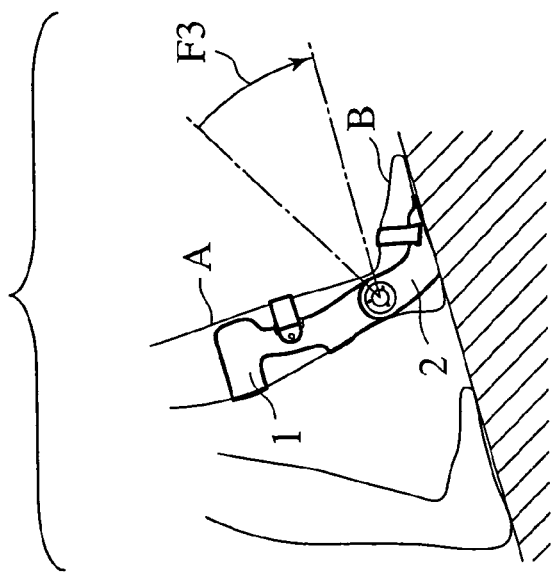
FIG. 8A is a view showing a state where both feet are set in line with each other in walking on an upward slope by the body orthosis of the first embodiment of the present invention.
Figure 8B:
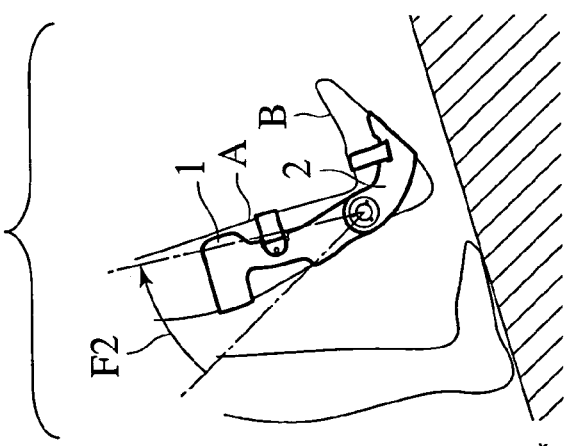
FIG. 8B is a view showing a state where the left foot is stepped forward in walking on the upward slope by the body orthosis of the first embodiment of the present invention.
Figure 8C:
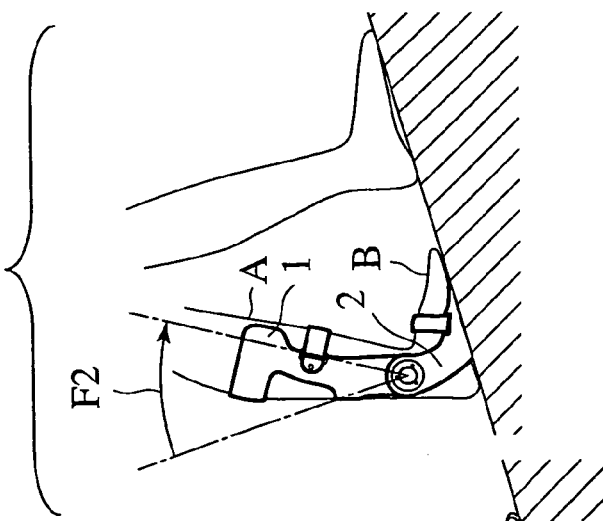
FIG. 8C is a view showing a state immediately before the right foot is stepped forward and landed in walking on the upward slope by the body orthosis of the first embodiment of the present invention.
Figure 8D:
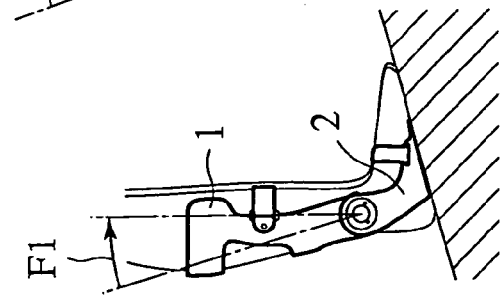
FIG. 8D is a view showing a landed state of the right foot stepped forward in walking on the upward slope by the body orthosis of the first embodiment of the present invention.

Next, description will be made for the case of walking on an upward slope (ascending slope). As shown in FIG. 8A, from a state where the left foot of the healthy side and the right foot wearing the body orthosis are in line with each other when seen from the side, specifically from a posture of the leg inclined forward by 15° (angle of F1 in FIG. 8A) from a vertical posture to both feet, the left foot of the healthy side is stepped forward. Then, as shown in FIG. 8B, the leg A of the right foot of the orthosis side is further inclined by 15° from the forward inclined posture to take a forward inclined posture of inclination of 30° (angle of F2 in FIG. 8D). In this case, a rotational load to the dorsiflexion side is 0 or near 0, and thus the facies posterior cruris cuff 1 can be rotated to match an angle of the leg A smoothly. Subsequently, when the right foot of the orthosis side is lifted from the ground to be stepped forward, as shown in FIG. 8C, the right foot can be moved while the posture immediately before the lifting (posture of the leg A of the right foot being inclined forward by 30°) is maintained. Accordingly, a toe of the right foot is prevented from drooping forward to be stubbed a toe against the ground. When the right foot lifted from the ground is landed on the ground, a load applied from the foot at the time of landing rotates the sole plate 2 to the plantar flexion side by 30° (angle of F3 in FIG. 8D), thereby changing the posture of the sole plate 2 so as to set its bottom surface parallel to the ground.

Lastly, description will be made for the case of walking on a downward slope. As shown in FIG. 9A, from a state where the left foot of the healthy side and the right foot wearing the body orthosis are in line with each other when seen from the side, specifically from a posture of the leg inclined backward by 15° (angle of G1 in FIG. 9A) from a vertical posture to both feet, the left foot of the healthy side is stepped forward. Then, as shown in FIG. 9B, the leg A of the right foot of the orthosis side is inclined forward from the backward inclined posture to take a vertical posture against the ground. In this case, a rotational load to the dorsiflexion side is 0 or near 0, and thus the facies posterior cruris cuff 1 can be rotated to match an angle of the leg A smoothly. Subsequently, when the right foot of the orthosis side is lifted from the ground to be stepped forward, as shown in FIG. 9C, the left foot can be moved while the posture immediately before the lifting (posture of the leg A of the right foot being vertical to the ground) is maintained. Accordingly, a toe of the right foot is prevented from drooping forward to be stubbed a toe against the ground. When the right foot lifted from the ground is landed on the ground, a load applied from the foot at the time of landing rotates the sole plate 2 to the plantar flexion side by 30° (angle of G2 in FIG. 9D), thereby changing the posture of the sole plate 2 so as to set its bottom surface parallel to the ground.

Figure 10A:
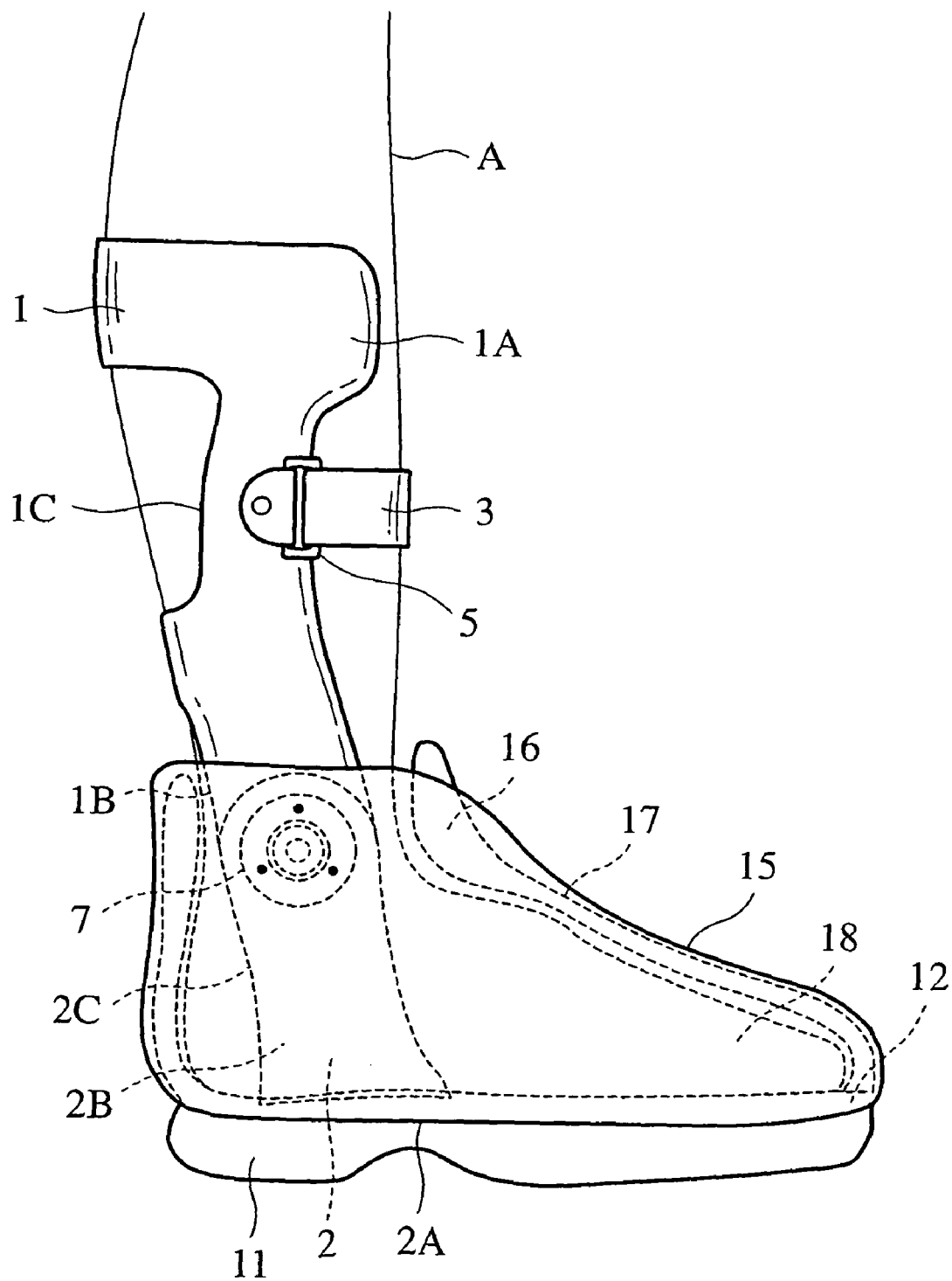
FIG. 10A is a side view showing a modified example of the first embodiment of the present invention.
Figure 10B:
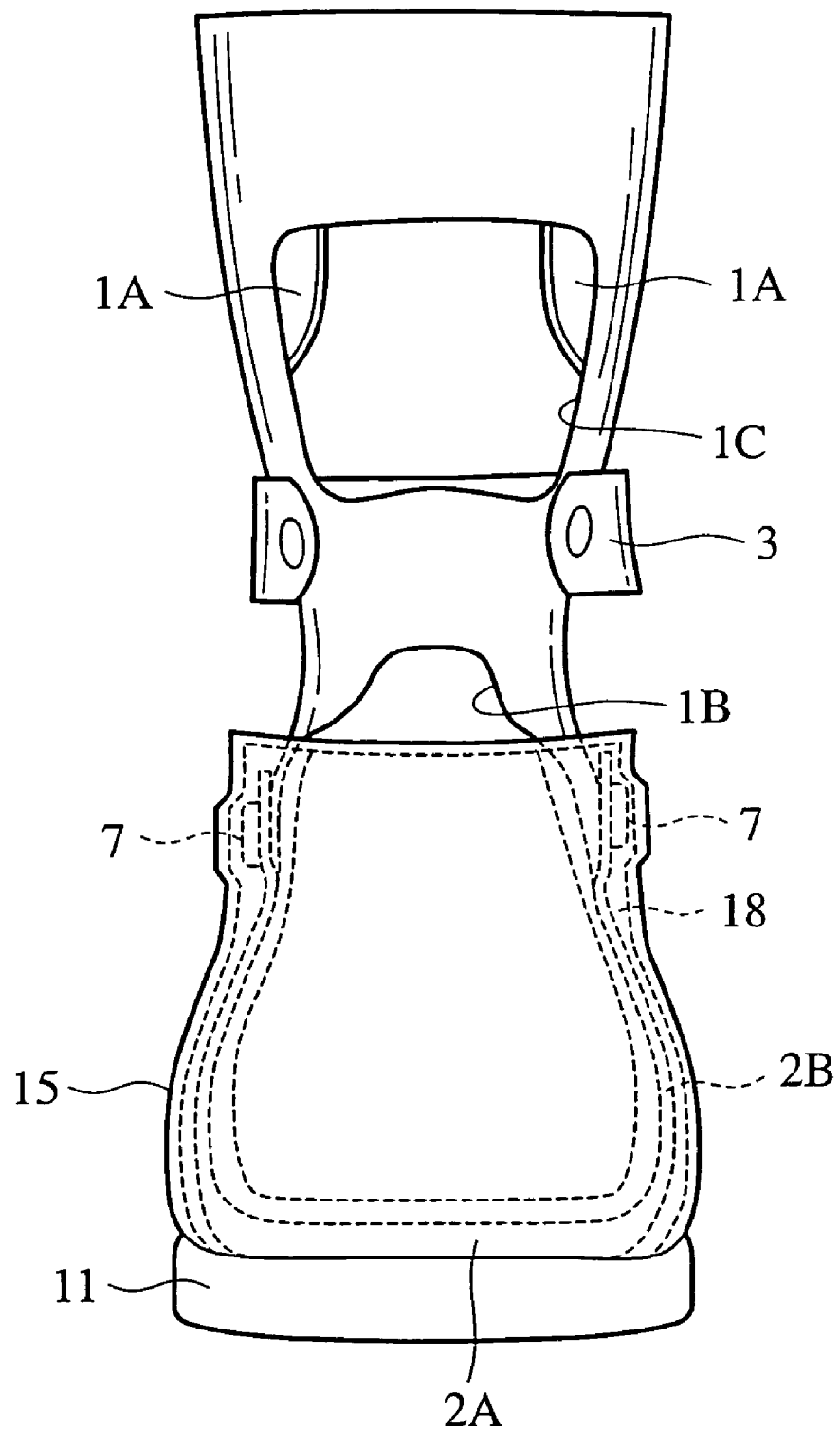
FIG. 10B is a rear view showing the modified example of the first embodiment of the present invention.

FIGS. 10A and 10B are side views showing a body orthosis of a modified example of the first embodiment described above. In the modified example, a portion below the outer side member 7 in the first embodiment is provided integrally with a shoe 15.

In the modified example, the belt 4 as the fixing member is omitted, because a foot is fixed by front and tongue cuir portions 17 and 16 of the shoe 15. A cord, stretching rubber or the like may be provided in the front cuir portion 17, thereby fixing an instep of the foot. A flared portion 2B is provided beforehand along an inner portion 18 inside the shoe. Similarly, a loading portion 2A is integrated with an inner bottom portion 12 or a sole portion 11 inside the shoe. In this case, the loading portion may be fixed by a screw or the like.

Other components are substantially similar to those of the foregoing first embodiment, and thus overlapped description thereof will be omitted. In the modified example, the portion formed integrally with the shoe was substantially below the calf. However, the flared portion 1A and the shape of the lower limb cuff 1 may be properly adjusted according to a type of a shoe or use. Moreover, an opening for adjustment may be provided in the shoe for adjustment by rotational load adjusting means.

When a shoe or the like was put on after loading of the first embodiment, the shoe became narrower inside by an amount equivalent to a thickness of the flared portion 2C or the loading portion 2A, and in addition the shoe and the body orthosis were separate. This arrangement was therefore inconvenient for exercise. According to the modified example, the flared portion and the loading portion are housed beforehand in the shoe, and thus uncomfortable feeling is reduced in exercise or the like. Moreover, since the outer side member 7 is housed in the shoe, a connected portion is protected.

Second Embodiment

Figure 11A:
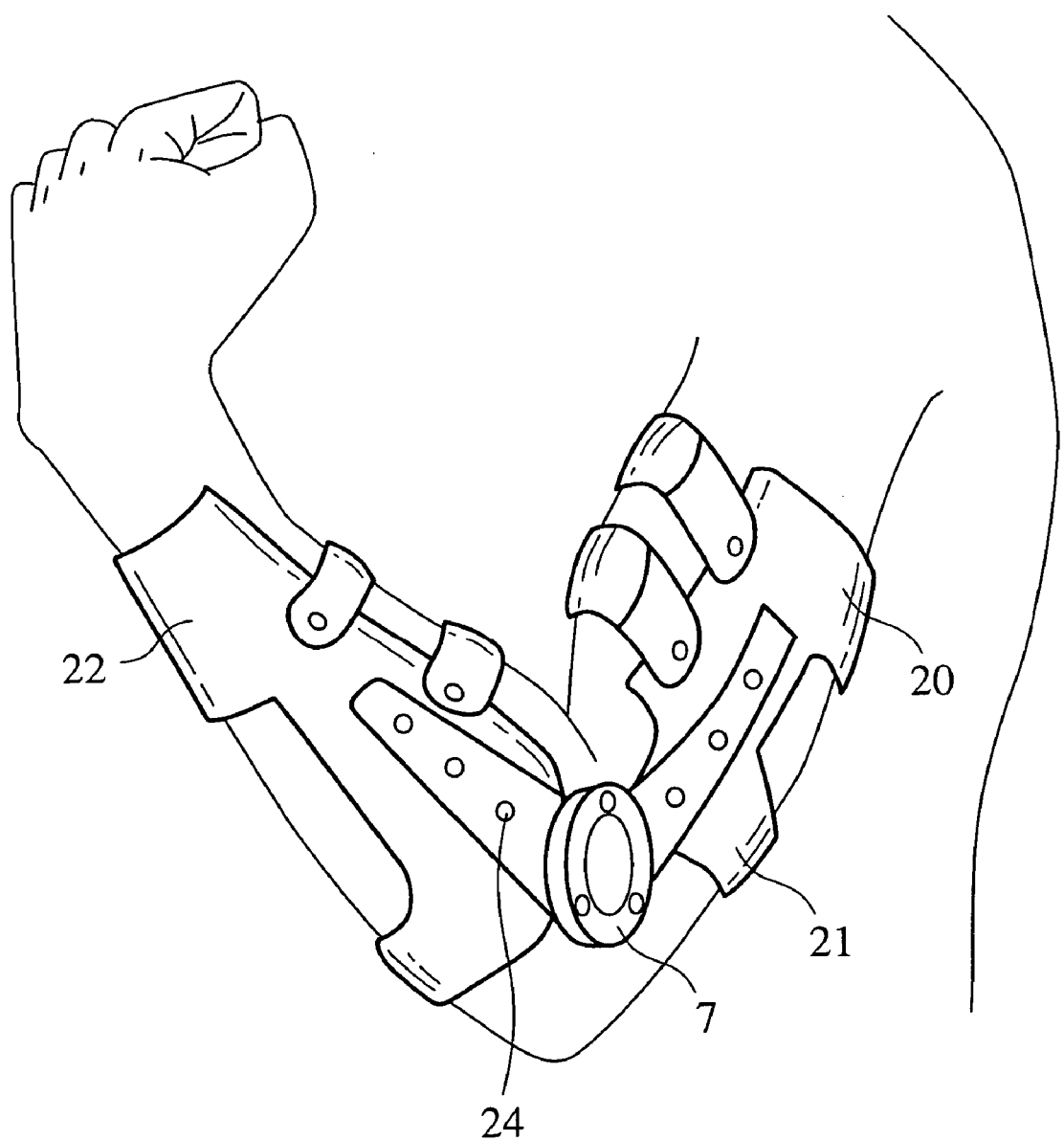
FIG. 11A is a perspective view of a second embodiment of the present invention attached to an arm portion.

FIGS. 11A to 11C show a second embodiment of the present invention.

A body orthosis 20 includes a cuff 21 having a pair of left and right flared portions 21A and 21A for protecting a rear part of an upper arm portion, a front arm cuff 22 similarly having a pair of left and right flared portions 22A and 22A for protecting a rear part of a front arm portion. The body orthosis 20 is bent in a circular-arc shape. The cuffs 21 and 22 of the upper and front arm portions are connected to each other so as to be rotated around a horizontal axial center substantially from a cubital fossa to an elbow. In this case, the outer side member 7 and the inner member 6 are connected to each other by connecting members 25A and 25B respectively for the upper and front arm cuffs 21 and 22. Then, the two connecting members 25A and 25B are respectively fixed to the cuffs 21 and 22 by screws 29 or the like.

Moreover, by four belts 23A to 23D provided in the body orthosis 20, upper and front arms can be fixed to the body orthosis 20. As in the case of the fixing belts 3 and 4 described above with reference to the first embodiment, fastening positions of the belts 23A to 23D as fixing members can be adjusted continuously. Note that the fixing members only need to fix the body orthosis 20, and the number thereof may be other than four, and made of cords or the like. Though not shown, adjustment may be made by using the metal fittings 5 or the like.

The cuffs 21 and 22 for the upper and front arms respectively are provided openings 27 and 28 formed on portions roughly on backsides of the upper and front arm portions. Accordingly, weight saving is realized. Other components are substantially similar to those of the first embodiment, and thus overlapped description thereof will be omitted.

According to the body orthosis 20 of the embodiment, different from a plaster cast or the like for simply fixing an arm portion, setting of a load is properly adjusted to provide a body orthosis, which matches a condition of a user.

Third Embodiment

FIGS. 12A to 12D show a body orthosis according to a third embodiment of the present invention.

Figure 12A:
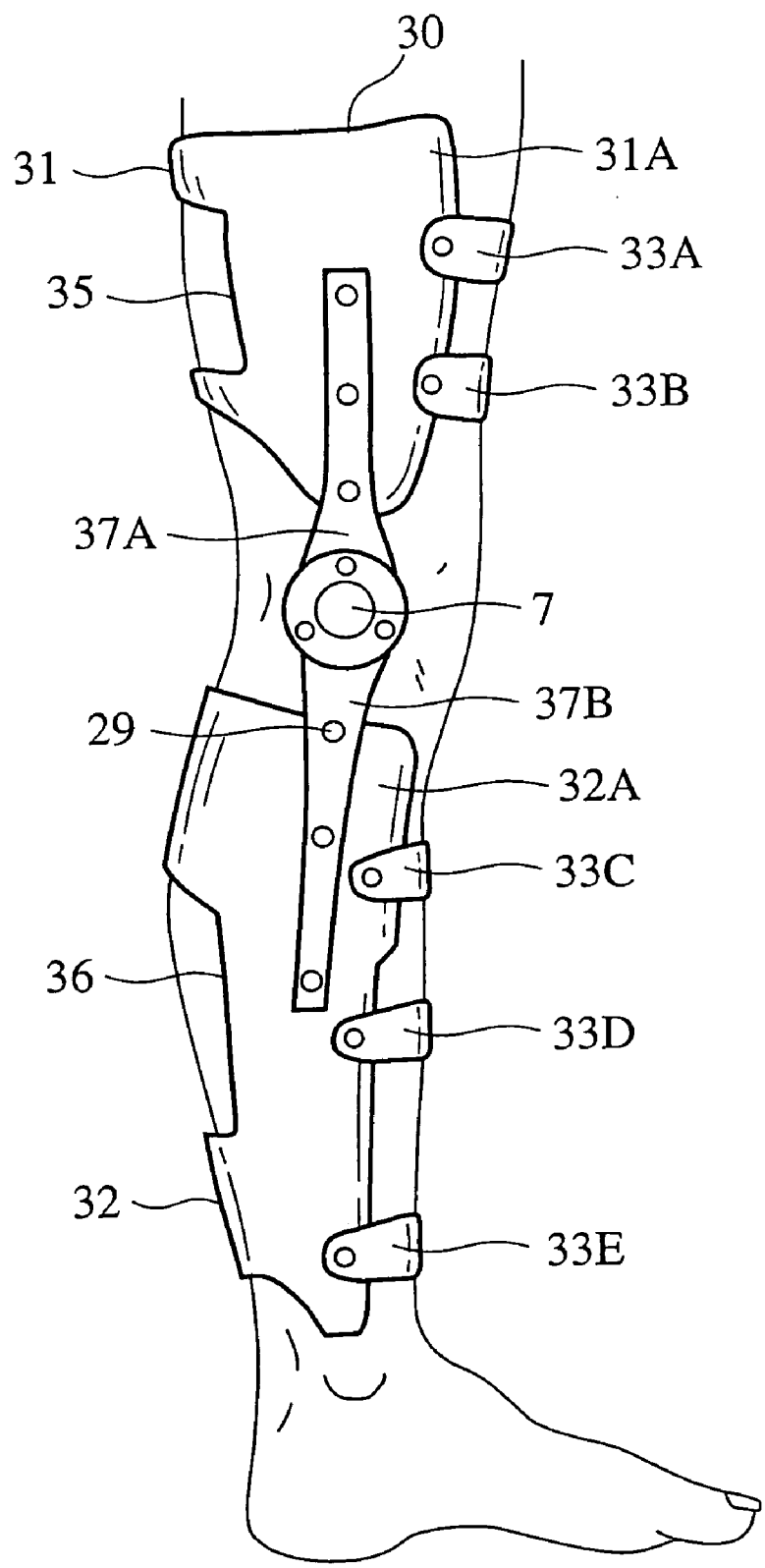
FIG. 12A is a side view of a third embodiment of the present invention attached to a leg portion.
Figure 12B:
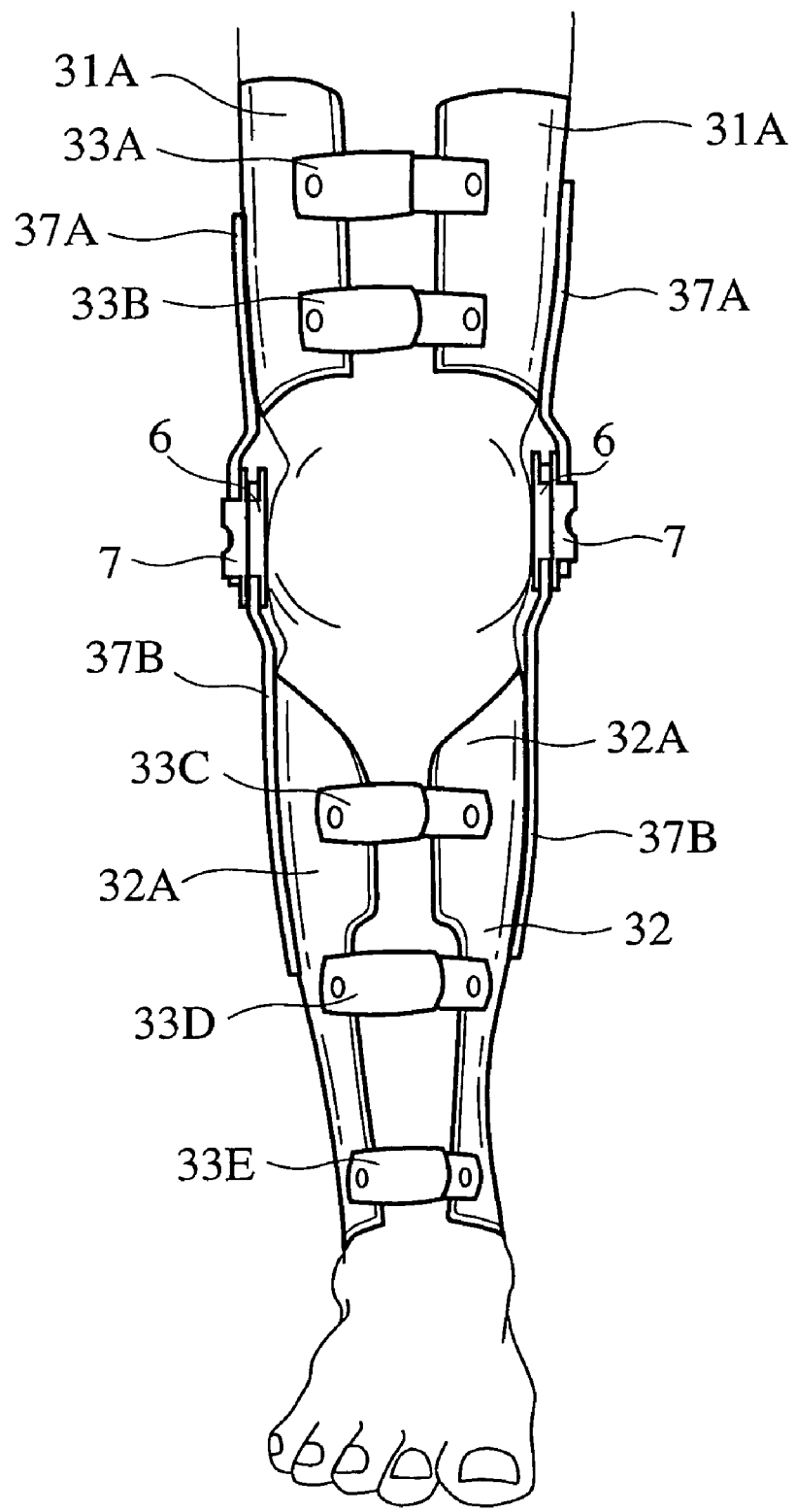
FIG. 12B is a front view showing the third embodiment of the present invention.
Figure 12C:
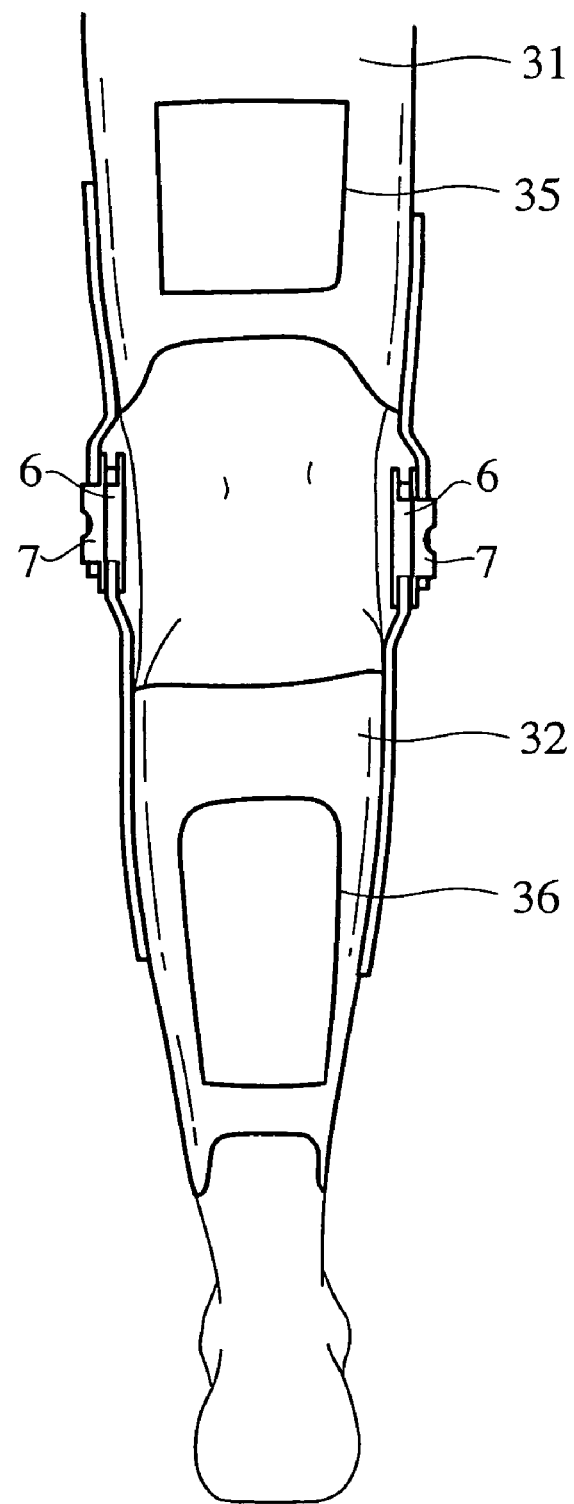
FIG. 12C is a rear view showing the third embodiment of the present invention.

FIG. 12A is a side view showing a body orthosis 30 of the embodiment. The body orthosis 30 includes a thigh cuff 31 having a pair of left and right flared portions 31A and 31A for protecting a rear part of a thigh portion, and a lower thigh cuff 32 similarly having a pair of left and right flared portions 32A and 32A for protecting a rear part of a lower thigh. The body orthosis 30 is bent in a circular-arc shape. The cuffs 31 and 32 for the thigh and lower thigh portions are connected to each other so as to be rotated around a horizontal axial center substantially from a knee fossa to a knee. In this case, the outer side member 7 and the inner member 6 are connected to each other by connecting members 37A and 37B respectively for the thigh and lower thigh cuffs 31 and 32. Then, the two connecting members 37A and 37B are respectively fixed to the cuffs 31 and 32 by screws 29 or the like. By five belts 33A to 33E provided in the body orthosis 30, the lower thigh and thigh portions can be fixed to the body orthosis 30. Though not shown, adjustment may be made by using the metal fittings 5 or the like. The cuffs 31 and 32 for the thigh and lower thigh portions respectively are provided openings 35 and 36 formed on portions roughly on a backside of the thigh portion and around the calf. Thus, weight saving is realized.

Figure 12D:
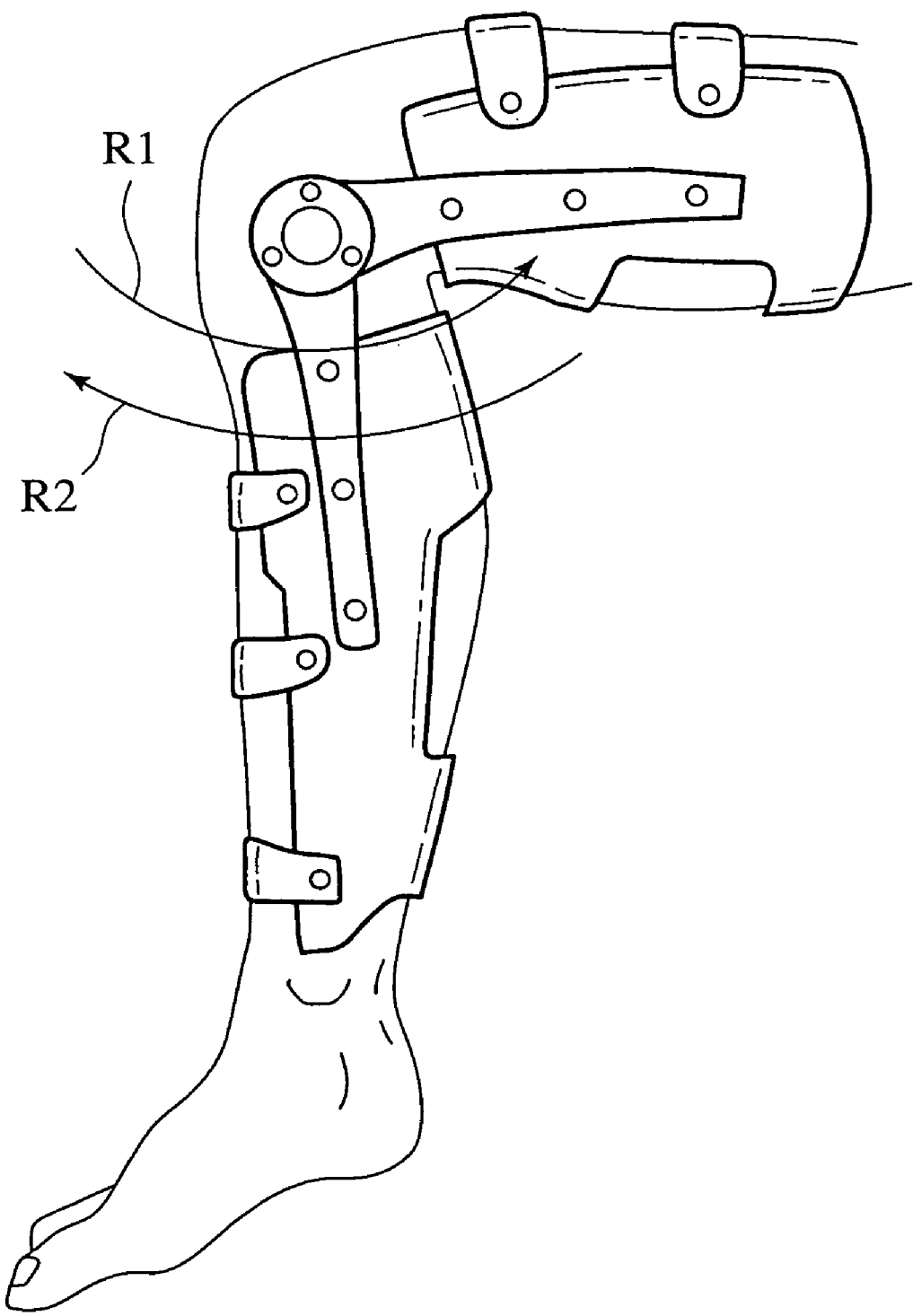
FIG. 12D is a view showing setting of a load according to the third embodiment of the present invention.

For example, in the body orthosis 30, as shown in FIG. 12D, a rotational load is set roughly equal to 0 when a knee portion is bent in one rotational direction R1. When the knee portion is bent in an opposite rotational direction R2, a rotational load is set larger than that in the direction R1. According to these settings, for example in the case of ascending the stairs, when a foot wearing the body orthosis 30 in an opposite side is lifted with a foot of a healthy side set as a support, since the load of the direction R1 is roughly 0, the knee portion can be naturally bent to a position sufficient for ascending the stairs following bending of the thigh portion. Then, until the foot wearing the body orthosis 30 reaches a next step of the stairs by weight movement with the foot of the healthy side set as a fulcrum, an angle of the knee portion can be maintained in the above-described position since the load of the rotational direction R2 is set large. After the weight movement, when the foot wearing the body orthosis 30 reaches a stair surface, the body orthosis 30 is rotated by a part of a load applied to the leg portion.

As described above, by using the body orthosis 30 of the third embodiment, not only in normal walking but also exercise where a load larger compared with walking on a flat land, such as ascending/descending of the stairs, is applied to one knee, walking can be assisted, and shocks can be absorbed.

The body orthosis of the first embodiment may be attached to the ankle, and that of the third embodiment may be used for the knee. Other components are substantially similar to those of the first embodiment, and thus overlapped description thereof will be omitted.

Furthermore, the body orthosis of the present invention can be applied to a joint connecting portion such as a wrist or a shoulder other than the foregoing embodiment. The shape and specific constitution of the body orthosis can be properly changed freely.

INDUSTRIAL APPLICABILITY

According to the present invention, by setting a rotational load to the plantar flexion side larger than that to the dorsiflexion side, when the landed foot is lifted, the foot can be held by the body orthosis at an angle of the foot-immediately before the lifting. Accordingly, it is possible to not only prevent the drooping of the toe to be stubbed against the ground simultaneously with the lifting of the food, but also make light and smooth rotation to the dorsiflexion side. A load applied by a part of weight caused by the landing of the foot is converted into a rotating force for rotating the body protective member. Accordingly, even when a large rotational load is set, plantar flexion hitherto impossible can be carried out by smoothly rotating the body protective member. Therefore, not only on the flat land but also on slopes (upward and downward), and any other places (changing situation of road surface) for walking from the flat land to the slope, from the slope to the flat land and the like, it is possible to provide a body orthosis for enabling walking of a near natural state to be carried out while plantar flexion or dorsiflexion is executed smoothly.

According to the present invention, by a load applied at the time of landing the sole plate, the sole plate is rotated so as to set its bottom surface parallel to the ground, and a rotational load is set so as to maintain the sole plate and the leg protective plate in states immediately before lifting when the sole plate is lifted. Thus, it is possible to construct a body orthosis to be handled much more easily, which can not only prevent contact of the toe with the slope to stumble when the foot is lifted, but also smoothly rotate the sole plate by a load (a part of weight) applied at the time of landing.

According to the present invention, the calcaneus portion in the rear side of the sole plate and the Achilles' tendon portion in the lower end rear side of the facies posterior cruris cuff 1, which cause no problems in strength, are formed to be open. Accordingly, not only weight becomes light, but also the shoe can be easily put on. Moreover, flexibility of the sole plate and the facies posterior cruris cuff can be also adjusted, making the body orthosis compatible to a patient.

According to the present invention, by setting the rotational center of the facies posterior cruris cuff substantially equal to the upper-and-lower height position of the foot joint axis of hominal physiology, the foot joint axis of the human body can be brought into rough coincidence with the rotational center of the facies posterior cruris cuff or the rotational center of the sole plate. Thus, the foot joint axis of the human body can be moved more easily, making the body orthosis much easier to be handled.

According to the present invention, by forming an opening in the center of the upper and lower sides of the facies posterior cruris cuff, weight saving can be further realized, and flexibility can be improved. Thus, it is possible to construct a body orthosis optimal for any patients.

According to the present invention, the fixing member is provided to fix the human body to the facies posterior cruris cuff or the sole plate over the left and right front ends of the facies posterior cruris cuff or the left and right upper ends of the sole plate. Accordingly, it is possible to prevent falling-off of the body orthosis in walking, thereby offering facilitating walking advantage.

According to the present invention, the rotational load setting means is constituted of an one-way bearing provided in the rotary shaft portion of the rotatably constructed body protective member. Accordingly, a rotational load to one side (e.g., dorsiflexion side) can be removed as much as possible, and a rotational load to the other side (e.g., plantar flexion side) can be set to a size for preventing rotation of the sole plate caused by the weight of the foot placed on the sole plate. Thus, walking can be made more much more natural (smoother).

According to the present invention, a rotational load to one side (e.g., dorsiflexion side) can be removed as much as possible, and a rotational load to the other side (e.g., plantar flexion side) can be set to a size for preventing rotation of the sole plate caused by the weight of the foot placed on the sole plate. Thus, it is possible to provide a body orthosis having no limitations on dorsiflexion or plantar flexion, and enabling walking to be carried out in a much more natural state.

The body orthosis of the present invention may be installed beforehand in the shoe. Since the loading portion or the like are housed beforehand in the shoe, the body orthosis can even be used for exercise or the like.

According to the present invention, the body orthosis can be constructed in such a manner that the protective plates of the upper and front arm portions are connected to each other by the rotational load setting means. Thus, by setting one rotational load larger compared with the other rotational load, it is possible to provide a body orthosis for an elbow, which matches a condition of the user.

According to the present invention, the body orthosis can be constructed in such a manner that the protective plates of the thigh and the lower thigh are connected to each other by the rotational load setting means. Thus, by setting one rotational load larger compared with the other rotational load, it is possible to provide a body orthosis for a knee, which can properly compensate for the bending of the knee in ascending/descending of the stairs or the like, and prevent stumbling or the like.

What is claimed is:

1. A body orthosis having a pair of body protective members adjacent to each other in a vertical direction, in which one of the body protective members is rotatable with respect to the other body protective member, the body orthosis comprising:
   rotational load setting means for setting a rotational load in one rotational direction of the rotatably constructed body protective member larger than a rotational load in the other rotational direction,
   wherein the rotational load setting means includes a one-way bearing provided in a rotary shaft portion of the rotatably constructed body protective member,
   wherein the body orthosis includes a sole plate for loading and supporting at least a part of a sole, and a leg protective plate for protecting at least a part of a leg, and side ends adjacent to these plates are connected to each other by the rotational load setting means, and
   wherein in the case of walking by using the body orthosis, the sole plate is rotated by a load applied at the time of landing the sole plate so as to set its bottom surface parallel to the ground, and when the sole plate is lifted, a size of the rotational load is set so as to maintain the sole plate and the leg protective plate in states immediately before the lifting.

2. The body orthosis according to claim 1, wherein the leg protective plate includes a facies posterior cruris cuff for protecting a calf and a calcaneus portion in the rear side of the sole plate and an Achilles' tendon portion in a lower end rear side of the facies posterior cruris cuff are formed to be open type.

3. The body orthosis according to claim 2, wherein a rotational center of the facies posterior cruris cuff is set at a height substantially equal to an upper-and-lower position of a foot joint axis of hominal physiology.

4. The body orthosis according to claim 2, wherein an opening is formed in a center of upper and lower sides of the facies posterior cruris cuff.

5. The body orthosis according to claim 2, wherein a fixing member is provided to fix a human body to the facies posterior cruris cuff or the sole plate over left and right front ends of the facies posterior cruris cuff or left and right upper ends of the sole plate.

6. The body orthosis according to claim 1, wherein the leg protective plate includes a facies posterior cruris cuff for protecting a calf, and a calcaneus portion in the rear side of the sole plate and an Achilles' tendon portion in a lower end rear side of the facies posterior cruris cuff are formed to be open type.

7. The body orthosis according to claim 1, wherein the rotational load setting means is positioned at a rotational joint between the body protective members.

8. A body orthosis comprising:
   a sole plate for loading and supporting at least a part of a sole;
   a leg protective plate for protecting at least a part of a leg; and
   a one-way bearing provided in a rotary shaft portion of the leg protective plate to rotate the sole plate by a load applied at the time of landing the sole plate so as to set its bottom surface parallel to the ground in walking, and maintain the sole plate and the leg protective plate in states immediately before lifting when the sole plate is lifted.

9. Rotational load setting means for a body orthosis comprising:
   an outer side member having a circular concave portion inside;
   an inner side cylindrical member having a circular convex portion fitted in the outer side member;
   a circular one-way bearing inserted into a portion held between the concave and convex portions of the two members;
   a stopper portion fitted to the one-way bearing and a disk portion provided in the inner side cylindrical member; and
   a screw penetrates a screw hole provided in the stopper portion and a screw hole provided in the outer side member.

10. The rotational load setting means for a body orthosis according to claim 9, wherein the stopper portion has a protruded portion, and is fitted in a long groove provided in the disk portion of the inner side cylindrical member.

* * * * *